United States Patent [19]
Edell et al.

[11] Patent Number: 5,078,137
[45] Date of Patent: * Jan. 7, 1992

[54] APPARATUS FOR MEASURING OXYGEN PARTIAL PRESSURE AND TEMPERATURE, IN LIVING TISSUE

[75] Inventors: David J. Edell, Lexington, Mass.; Stephen K. Burns, Henneker, N.H.; Harry F. Bowman, Needham; James C. Weaver, Sudbury, both of Mass.

[73] Assignee: Massachusetts Institute of Technology, Cambridge, Mass.

[*] Notice: The portion of the term of this patent subsequent to May 3, 2005 has been disclaimed.

[21] Appl. No.: 859,453

[22] Filed: May 5, 1986

[51] Int. Cl.$^5$ .................................................. A61B 5/00
[52] U.S. Cl. .................................. 128/635; 128/736; 204/403; 204/408
[58] Field of Search ............... 128/635, 736; 204/403, 204/408, 431

[56] References Cited

U.S. PATENT DOCUMENTS

| | | | |
|---|---|---|---|
| 4,062,750 | 12/1977 | Butler | 204/403 X |
| 4,301,807 | 11/1981 | Mentelos | 128/635 |
| 4,582,064 | 4/1986 | Sorger | 128/635 |

FOREIGN PATENT DOCUMENTS

| | | | |
|---|---|---|---|
| 2836883 | 3/1980 | Fed. Rep. of Germany | 128/635 |
| 2943958 | 5/1981 | Fed. Rep. of Germany | 128/635 |

OTHER PUBLICATIONS

Butler et al., "A Multicathode Oxygen Sensor . . . ", 5th Can. Med & Biol. Eng. Conf., Montreal, Canada, Sep. 1974, p. 5.29-b.

*Primary Examiner*—Lee S. Cohen
*Attorney, Agent, or Firm*—Paul J. Cook

[57] ABSTRACT

A probe adapted for insertion in living tissue for measuring oxygen partial pressure and temperature at a plurality of sites in living tissue is provided. A temperature sensitive resistor is positioned adjacent each of a plurality of oxygen sensors so that the oxygen partial pressure measured can be adjusted for tissue temperature. The probe substrate has thermal properties similar to living tissue and the resistors are formed of a material having a temperature sensitive resistance. Temperature at each temperature sensitive resistor is obtained by measuring resistance with a four point measurement and correlating the resistance to temperature.

7 Claims, 7 Drawing Sheets

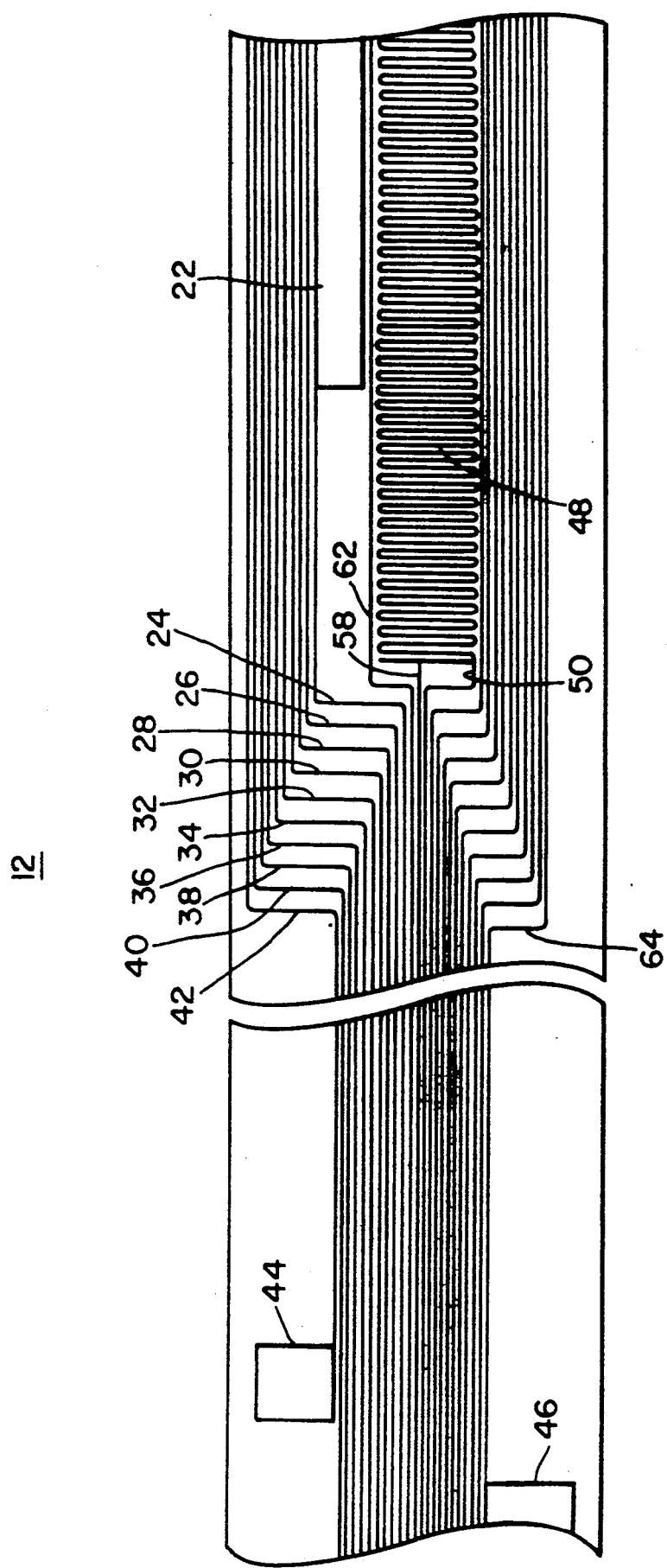

APPARATUS FOR MEASURING OXYGEN PARTIAL PRESSURE AND TEMPERATURE, IN LIVING TISSUE

The government has rights in this invention pursuant to Grant No. CA37235 awarded by the National Institute of Health-National Cancer Institute.

BACKGROUND OF THE INVENTION

This invention relates to a method and apparatus for determining oxygen partial pressure ($PO_2$) and temperature simultaneously in living tissue at multiple sites of the tissue. particularly, this invention relates to such an apparatus which can also determine thermal conductivity, thermal diffusivity, SAR (Specific Absorption Rate) and blood perfusion in the living tissue at multiple sites.

Interest in the fundamental mechanisms of heat transfer in living tissue and in accurate clinical thermometry derives from the fact that many patients with malignancies who failed surgery, radiation and/or chemotherapy are responsive to the local application of heat resulting in elevated tumor temperatures. Well-managed clinical application of hyperthermia requires the ability to produce specific, well-characterized temperature elevations in precisely selected volumes of tissue that comprise the malignancy. The corresponding engineering requirement is the ability to control the temporal and spatial characteristics of the absorbed thermal dose so as to produce the desired temperature distribution for the specific malignanc being treated.

The achievement and accurate measurement of the elevated temperature distribution is thus of primary importance in any hyperthermia system. The existence of computerized axial tomography makes three-dimensional visualization of tissue densities possible, and contrast angiography can also be used to map the vasculature in the tissue volume. However, neither produces temperature or oxygen images. In terms of hyperthermia heating means, microwave, radio-frequency currents and ultrasound have been used as non-invasive sources of volumetric heat generation in tissue. Each of these three heat source means has specific advantages and limitations. An ideal system would provide control of the temporal and spatial characteristics of the heat source in order to shape the volumetric power deposition pattern to the specific requirements of the tumor mass.

In view of the rather significant tissue temperature gradients that can exist as a consequence of differential blood flow and thermal conductivity (both of which are enhanced with increased perfusion in surrounding tissue) and the clear evidence that even a small difference in temperature level could be crucial to the success of hyperthermia, it is equally crucial that good thermometry be available. Since the temperature gradient will be largest at boundaries of differential energy absorption, perfusion and/or conductivity, it is important that the temperature at the tumor margin or proliferating edge be known. It could well be that the apparent resistance of some tumor peripheries to hyperthermia is really due to inadvertent sublethal heating due to lack of adequate thermometry at the tumor boundaries. It is the lowest temperature in the tumor and the highest temperature in the normal tissue that is limiting in the management of tumors by hyperthermia.

The state of tissue perfusion is a primary factor in local transport of heat, the regulation of which is clearly crucial for hyperthermia; of drugs, the delivery of which is crucial in chemotherapy; and of oxygen and nutrients which are known to be important for effective radiation therapy. Thus, optimization of each of these individual cancer therapies (or synergism through combined use) each requires knowledge of the distribution and magnitude of the local level of perfusion. Differences in perfusion rates between the core and periphery of rapidly growing tumors have been found using a number of techniques, including the embedded thermistor probe (Holmes et al., *ASME Advances in Bioengineering*, pp. 147-149,1979). Because blood flow is known to have a dramatic influence on the temperature distribution in tissue during hyperthermia, knowledge of the magnitude and the distribution of perfusion in both the tumor and surrounding host tissue is necessary for accurate thermal therapy planning and for directing the local deposition of heat to produce uniform temperature elevations over the desired region.

There also appear to be a few important difference between blood flow in tumor and normal tissue which include: the character and distribution of the vasculature, as well as the ability to increase local perfusion in response to thermal stress at various levels and durations of local hyperthermia. Normal tissue such as skin can increase blood supply as much as seven times in response to elevated temperatures of 42-43° C. This responsive cooling mechanism has been observed as reductions in measured temperatures during hyperthermia and must be taken into account when calculating local power requirements.

Copending U.S. patent application Ser. No. 730, 614, now U.S. Pat. No. 4,741,343, discloses a probe adapted to measure oxygen partial pressure and temperature in body tissue. The probe utilizes discreet thermistors for measuring temperature which requires individual placement of the thermistors on the probe substrate thereby complicating the fabrication process. In addition, this probe does not permit a four point measurement process so that the measurements obtained are undesirably dependent upon the resistance of the leads to the thermistors. In addition, the thermistors protrude from the probe surface thereby increasing the possibility that they will be damaged when the probe is inserted into tissue. Because of the discrete thermistor construction, which makes substantial amounts of gold, the thermal conductivity of the thermistor probe does not match tissue. This will create disturbances in the thermal gradients of interest.

It would be desirable to monitor temperature distributions accurately during hyperthermic treatments of cancer while minimally perturbing the local thermal environment. Furthermore, it would be desirable to provide a means for obtaining these measurements at a plurality of tissue locations as well as other measurements of tissue characteristics including blood perfusion, thermal conductivity and thermal diffusivity.

In addition, determination of the spatial distribution of $PO_2$ in ionizing radiation therapy of tumors is important. Regions of tumors with low $PO_2$ do not respond adequately to ionizing radiation therapy. Therefore, direct assessment of the spatial distribution of $PO_2$ in tumors is useful in establishing whether or not radiation therapy will be successful or whether or combined radiation/hyperthermia therapy will be needed. In order to be accurate, $PO_2$ measurements at multiple sites must each be temperature compensated, thereby requiring a temperature measurement at each site.

SUMMARY OF THE INVENTION

In accordance with this invention, a monolithic probe having an integrated thin film array of temperature sensitive resistors and oxygen sensors adapted for insertion in living tissue is provided, which contains a plurality of resistors in series which have an electrical resistance dependent on temperature had a plurality of oxygen sensors. The probe is formed from a substrate that has thermal properties similar to tissue into which it is to be inserted. Each of the oxygen sensors is positioned adjacent to a resistor, and all of the oxygen sensors are connected by electrically conducting paths to means for correlating electrical current or voltage to oxygen partial pressure. Means are provided for passing an electrical current through one or more of the temperature sensitive resistors and for measuring voltage drop across each resistor. Means are also provided for heating one or more temperature sensitive resistors and correlating the thermal response with perfusion. These measurements also can be correlated with thermal conductivity, thermal diffusivity, and specific thermal absorption rate of the tissue surrounding the probe.

DESCRIPTION OF SPECIFIC EMBODIMENTS

Figure 1:
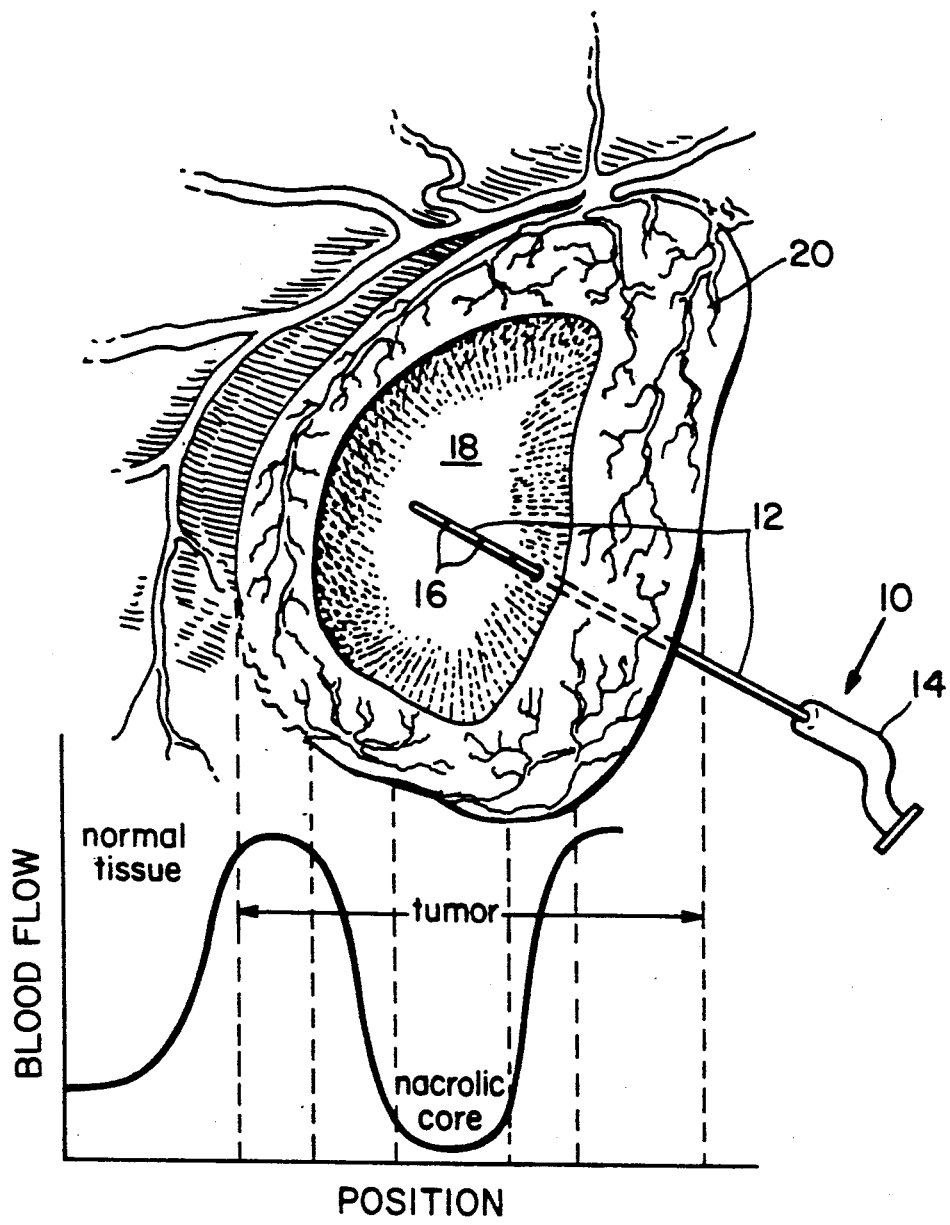
FIG. 1 is a cross sectional view of a tumor tissue having the probe of this invention inserted therein and representative blood flow as a function of tissue position.

In accordance with this invention, an apparatus is provided which includes a probe substrate having cross-section sufficiently small so that it can be inserted into living tissue, more specifically tumor tissue. The size of the probe substrate including its length and cross section, are arbitrary. The practical substrate cross-sectional dimension will be between about 100 amd 1,000 microns and the length will be between 0.5 and 20 centimeters. Materials are selected and the probe arrays are designed to provide a good thermal match to tissue. Temperature sensitive resistors and leads are fabricated as a single thin film which is patterned to form the thermally sensitive resistor and leads and the bases for the oxygen sensors along the length of the probe substrate to provide a plurality of positions wherein tissue temperature can be measured at each position. Temperature measurements are made at the site of each temperature sensitive resistor by passing an electrical current through one or more of the resistors and measuring the voltage drop across each of the resistors utilizing leads that are different from the current carrying leads. The temperature sensitive resistors are formed of a metal which exhibits a resistance as a function of temperature. The voltage drop is correlated to temperature by means outside the tissue being examined.

A plurality of oxygen sensors is also provided. Each of the oxygen sensors is positioned very closely, within 100 $\mu$m or less, to a single temperature sensitive resistor. The purpose of positioning the oxygen sensor close to a temperature sensitive resistor is than oxygen diffusivity and solubility in tissue is also temperature sensitive, so that in order to determine actual oxygen partial pressure, it is necessary that the temperature at the measurement site be known with sufficient accuracy, viz. $\pm 0.10$ C or less. Thus, the measurement of temperature at each of the resistor locations not only provides a temperature measurement, but provides a means whereby a suitable corrected oxygen partial pressure measurement can be obtained at each location of the oxygen sensors. Each of the oxygen sensors is also connected to a thin electrically conductive path which leads to a point outside the living tissue to means which correlate the electrical current flowing through each oxygen sensor with the oxygen partial pressure. At each site an oxygen measurement is made using one lead and a reference electrode is remotely located elsewhere in the tissue.

It is only necessary that a sufficient number of oxygen sensors, each associated with a temperature sensitive resistor, are provided so that oxygen partial pressure measurements can be obtained at a suitable number of sites within the tissue of interest. This is primarily of interest in cancerous tumor tissue or tissue study to assessment wherein it is necessary to know the oxygen partial pressure distribution within the tissue. For example, in radiation therapy the presence of oxygen in the tissue being radiated is necessary in order to render the radiation effective. If a diagnostician determines that there is insufficient oxygen present in the tissue to render radiation therapy effective, then alternative forms of therapy can be utilized. Since cancerous tumors vary widely in size, the number and spatial separation of oxygen sensors along the probe substrate also will vary accordingly. Generally, it is necessary to utilize at least two oxygen sensors, preferably between about five and about 20 oxygen sensors up to about 100 oxygen sensors spaced apart along the surface of the probe substrate. As noted above, each oxygen sensor must have associated with it a temperature sensitive resistor so that the oxygen sensor partial pressure measurement obtained can be adjusted to account for the effect of temperature in the tissue surrounding the oxygen sensor.

Each oxygen sensor and temperature sensitive resistor is connected to a means located outside the living tissue which translates the electrical currents and resistance to the desired physical parameters of oxygen concentration, temperature and derived quantities. The electrical connection is provided by a lead from each oxygen sensor and a lead from the reference electrode so that the current derived by virtue of oxygen molecule diffusion to the oxygen sensor can be measured. Temperature at each resistor is obtained by measuring resistance with a four point measurement and correlating the resistance measurement obtained with temperature. The four point measurement technique can be used with high resistance leads and has the following additional advantages: it renders the measurement independent of lead resistance, switch resistance and adjacent segment resistance. The measurement also is independent of contact resistance between bonding pads for external leads and the external leads.

The electrically conducting paths connected to the oxygen sensors and the temperature sensitive resistors pass along the probe substrate out of the tissue and are connected with means adapted to convert the electrical signals to oxygen partial pressure and temperature. Any conventional microprocessor, computer, analog circuit, computational device, table or the like can be utilized so long as it is constructed and programmed by means well known in the art to convert the electrical current measurements to oxygen partial pressure and temperature by taking into account the following parameters: oxygen electrode polarization potential, temperature of oxygen interface, oxygen electrode current, diffusion coefficient of oxygen in gradient near electrode, solubility of oxygen in the medium adjacent the electrode, geometry of oxygen electrode, temperature-resistance relationship and characteristic of the sensor. By providing an accurate measurement of oxygen partial pressure as a function of tissue location, which takes into account the effect of temperature, the person skilled in the art can utilize this miniature, minimally invasive means for determining whether therapeutic procedures, which rely upon the presence of oxygen in the tumor tissue, can be employed satisfactorily. Furthermore, since the apparatus of this invention provides accurate temperature measurement at distinctive separate locations within the tissue where the probe substrate is inserted, one can determine whether all or only a portion of tumor tissue being heat irradiated has achieved a sufficiently high temperature to be effective to kill the tumor tissue. As noted above, if a minimum temperature, usually between about 42.5 and 44° C., is not achieved continuously over the therapy time period, usually between about 20 and about 40 minutes then therapy will be ineffective since only a portion of the tumor tissue will be killed. If this occurs, the remaining living cells will continue to multiply rendering the therapy ineffective. Thus the present invention provides a means whereby heat radiation therapy to tumor tissue can be evaluated on a more local basis for efficacy. Such assessment will not be based on large average temperature measurements, but by distinct and separate temperature measurements showing the specific time-temperature conditions under which heat radiation therapy is or is not effective. Use of computation based on temperature, thermal conductivity, thermal diffusivity and perfusion obtained at measured sites permits prediction of tissue temperature at non-measured sites in the region of interest. When the measurement or prediction shows the therapy to be improper, the temperature of the therapy is changed and the radiation can be directed to portions of the tumor according to the measurements.

The apparatus of this invention also can be utilized to provide measurements of the characteristics of the tissue surrounding the probe substrate such as thermal conductivity, thermal diffusivity, perfusion and/or specific thermal absorption rate. Electrical current is supplied to the one or more resistors which are formed of a material having a resistance that is temperature dependent. The current to the temperature sensitive resistors is regulated by any conventional means such as an electronic control circuit. The voltage drop across each temperature sensitive resistor then is read by a readout device external the tissue which is connected by leads extending along the probe to the resistor. The readout device can be provided with means for reversing polarity of that any errors in the circuit, if any, can be added or subtracted from the output signal and is thereby determined. The signal can be connected to digital forms and can be used as digital input information to a data processor which is arranged to calculate thermal conductivity, thermal diffusivity, perfusion and specific thermal absorption rates. The means for determining thermal conductivity, thermal diffusivity and perfusion are disclosed, for example, in U.S. Pat. No. 4,059,982, which is incorporated herein by reference. Perfusion can be calculated by any means well known in the art such as those based on the bioheat equation or simplification thereof, for example as taught in U.S. Pat. No. 4,059,982. The specific thermal absorption rate (SAR) or local deposition of energy can be determined from the initial r slope of the temperature-time curve modified by multiplying by the product of tissue density and heat capacity c. The product is known from the ratio of thermal conductivity k to thermal diffusivity $a$; $pc = k/a$ Referring to FIG. 1, the apparatus of this invention 10 includes a probe substrate 12 and a handle 14 attached to the probe substrate 12 and through which conductive paths can be made for connection with electrical current processing means (not shown). The thermal probe includes a plurality of sensor sites, each of which sensor sites includes a temperature sensitive resistor and an oxygen sensor which is inserted into tumor tissue 18 and normal tissue 20. As shown in FIG. 1, blood flow through the normal tissue 20 and the tumor tissue 18 varies with position. Therefore, oxygen partial pressure, temperature, thermal conductivity, thermal diffusivity, blood perfusion and specific thermal absorption rate within the tissues 18 and 20 will vary with position.

Figure 2:
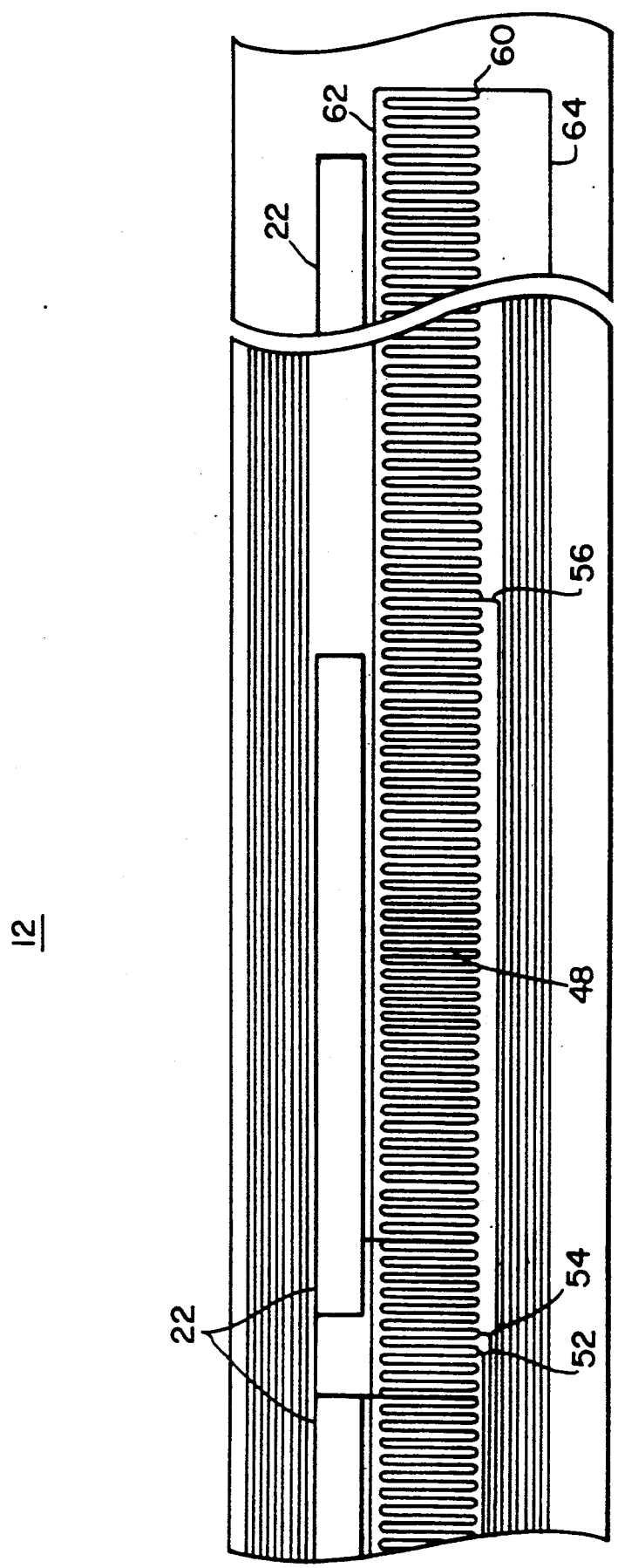
FIG. 2 is a top view of the probe of this invention.
Figure 3:
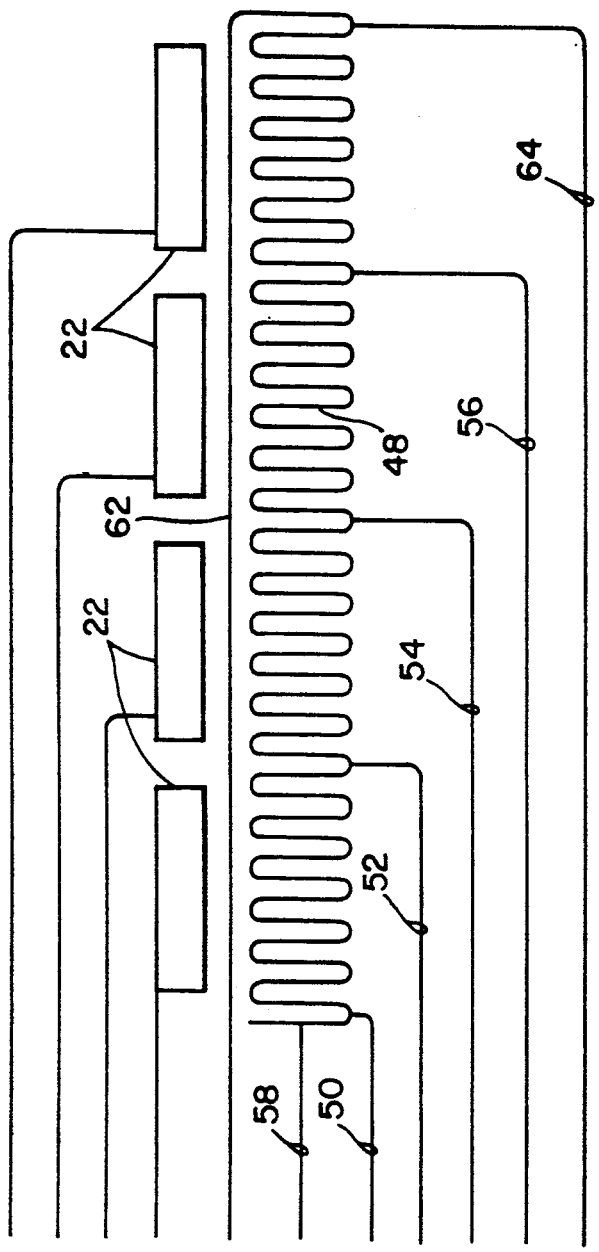
FIG. 3 is a schematic of the probe of this invention

As shown in FIGS. 2 and 3 the probe substrate 12 has bonded thereto a plurality of oxygen sensors 22, each of which is connected to a single oxygen partial pressure lead 24, 26, 28, 30, 32, 4, 36, 38, 40 or 42. Each of the oxygen leads is connected to a circuit external the tissue (see FIG. 6) by means of a bonding pad 4 or 46 or the like with one bonding pad being connected to one oxygen sensor 22. A centrally positioned serpentine conductive path 48 bonded to the probe substrate which is segmented by conductive resistor leads to form a plurality of temperature sensitive resistors in series. It is preferred to form the resistors from a metal having a relatively high resistivity in order to minimize interaction by the probe with microwave therapy. In addition, it is desirable that the metal forming the resistors exhibit a relatively large change in resistivity as a function of temperature, that it can be plated directly with a stable metal which is reactive with oxygen molecules, that does not migrate during use when plated as fine lines, that is stable when insulated and that can be deposited as a thin film in the order of about 100 Angstroms to about 1 micron thick. As shown in FIGS. 2 and 3, a first resistor comprises the portion of serpentine conductive path 48 positioned between resistor lead 50 and resistor lead 52 while a second resistor comprises the portion of serpentine conductive path 46 positioned between resistor leads 54 and 56. Current can be introduced through one or more leads, e.g. 50, 58, 52, 54, 56, or 64. Any of the resistor leads can be sensed and any can be excited. Thus, any one or set of segments can be used to create different thermal fields within the same environment. Hence, thermal diffusivity and conductivity can be derived. The programmable geometry for power dissipation in order to determine their properties comprises a significant advantage of this sensor design For example, current is introduced into the serpentine resistor path 48 by current leads 58 and 54 and thence to an external current measurement circuit. The voltage drop is measured on leads 58 and 54 for example by a voltmeter to obtain the resistance measurement.

Figure 4:
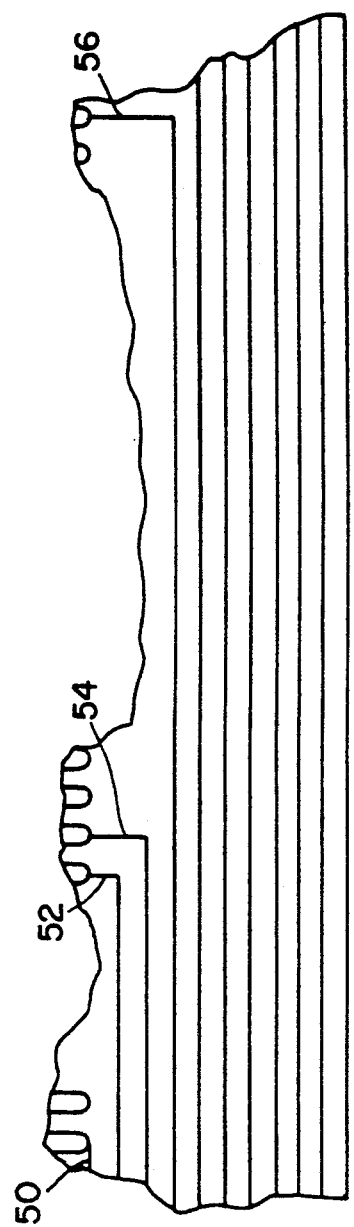
FIG. 4 is a more detailed view of the probe shown in FIG. 2.

As shown in FIG. 4, excitation and measurement apparatus is connected to leads emanating from the probe through a multiplicity of cross-point switches (such as the integrated cross-point switch circuit type CD22100 manufactured by RCA Corporation) which by appropriate command provides a conducting path at the intersections of the horizontal (58,50,52,54,56,62,64) and the vertical (71,72,73,74) leads. Since essentially no current is drawn by the sensing amplifier 75, the voltage measured is that developed by the electrical current through the sensed resistor and there is no error associated with a voltage drop in the measurement leads. Consider, for example, a situation in which a single segment is heated. Current source 70, connected to provide current through lead 7 connected to lead 50 by the intersection cross-point 80 and returning via lead 52, cross point 81 to lead 73. There is a voltage drop in lead 71, cross-point 80, in lead 50,52, cross-point 81, and return lead 73. One lead of the sensing amplifier, 75, is connected to the excited resistor segment through lead 72, crosspoint 82, lead 58, the unexcited adjacent resistor segment. The second input lead, 74, is connected through cross-point 83, lead 54, and the other unexcited adjacent resistance segment. Since no current flows through any of these paths, the voltage measured truly represents the potential at the junction of the excited resistance segment and leads 50 and 52. Alternatively, the entire series of resistances could be excited by closing cross-points 84 and 85 and selecting an individual segment.

Figure 8:
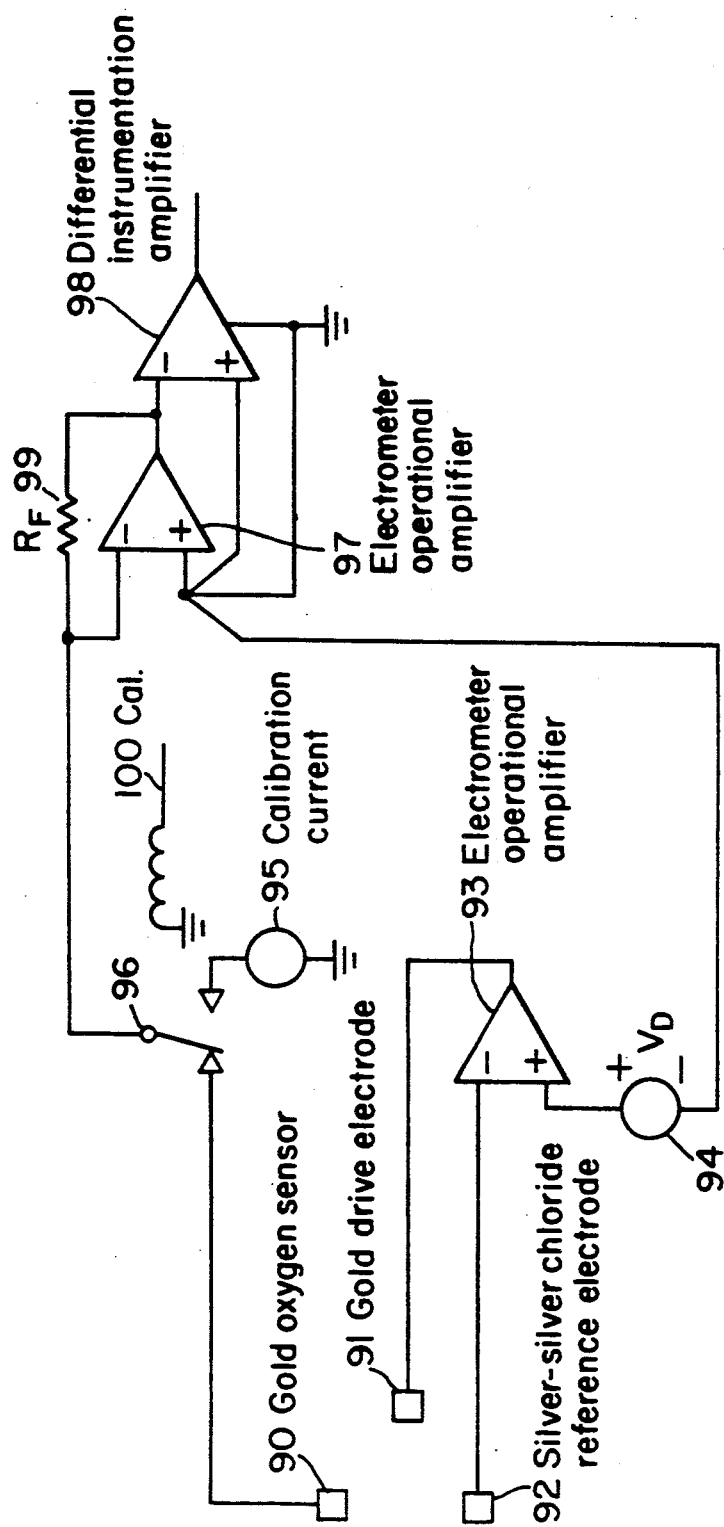
FIG. 8 shows a typical thermal sensor response of resistance as a function of temperature.

Referring to FIG. 8, oxygen produces a current which is conveyed to electrometer amplifier, 97, through the normally closed contacts of calibration relay 96. The oxygen sensor is polarized at $-V_D$ volts derived from controllable reference 94 with respect to silver-silver chloride reference electrode, 92. Essentially no current flows through this reference electrode (which might be used as a common reference for many sensing electrodes). Necessary return current is supplied through a gold drive electrode, 91, supplied by electrometer operational amplifier 93. This operational amplifier, 93, supplies sufficient current so as to constrain the silver-silver chloride reference electrode potential to equal the potential of the reference $V_D$, 94. The developed oxygen current conveyed to the input of electrometer amplifier 97 is balanced by an equal current flowing through feed-back resistor $R_F$,99, and develops an output voltage proportional to $R_F$ and the oxygen current. This voltage is applied to the inverting input or a differential instrumentation amplifier, 98, which provides a positive output voltage appropriately amplified for presentation to the data acquisition system. It additionally provides improved accuracy and noise rejection by measuring differentially the voltage developed between the output terminal of the electrometer amplifier, 97, and its non-inverting output terminal. Calibration ting a precisely known set of calibration currents, 95, for the oxygen current allowing automatic calibration of the measuring system.

Figure 6:
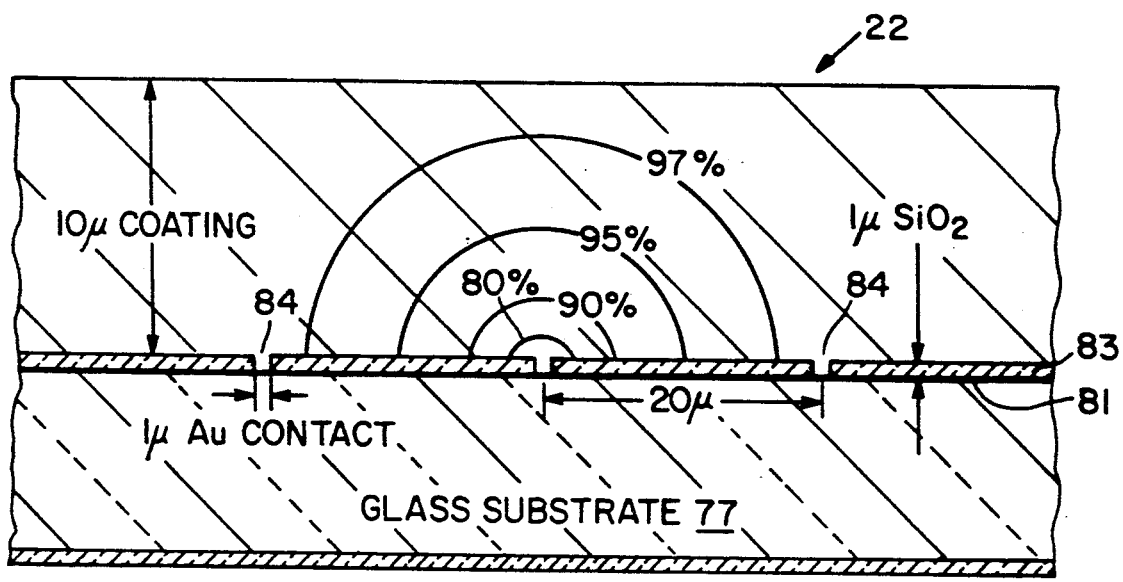
FIG. 6 represents the approximate predicted oxygen distribution about each contact on a microperforated oxygen electrode in steady state.

Referring to FIG. 6, the oxygen sensor 22 is formed of a substrate 77 such as glass which exhibits thermal conductivity similar to the tissue into which the probe 12 is implanted.

Figure 5:
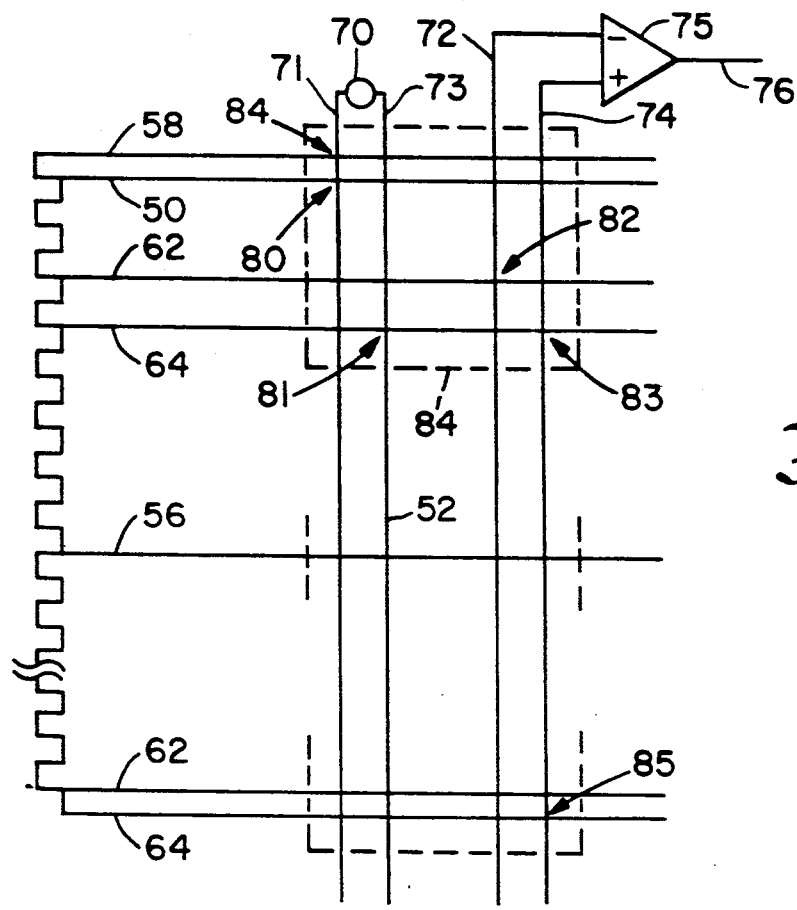
FIG. 5 shows the circuitry for four point measurement of resistors in the probe of FIG. 2.

A layer about 0.01 to $1\mu$ thick comprising a metal base such as nickel, molybedemum, titanium, tantalum or the like onto which is coated a metal which reacts with oxygen molecules such as gold, platinum, palladium or the like is adhered to the substrate 77 such as by sputtering, evaporation or electroplating. A dielectric layer such as $SiO_2$ or $Si_3N_4$ 83 then is applied to the gold layer 81 which then is perforated with a plurality of holes 84 of a size less than about 2 microns to expose the oxygen molecule reactive layer 81. The dielectric layer 83 as well as the entire surface of the probe having the sensors then is coated with a protective coating which is permeable to oxygen molecules such as agarose or gelatin or the like which is ionically conductive and has thermal properties similar to the surrounding tissue into which it is implanted. The approximate distribution of oxygen about each contact on the microperforated oxygen electrode in a steady state is illustrated in FIG. 5.

Figure 7:
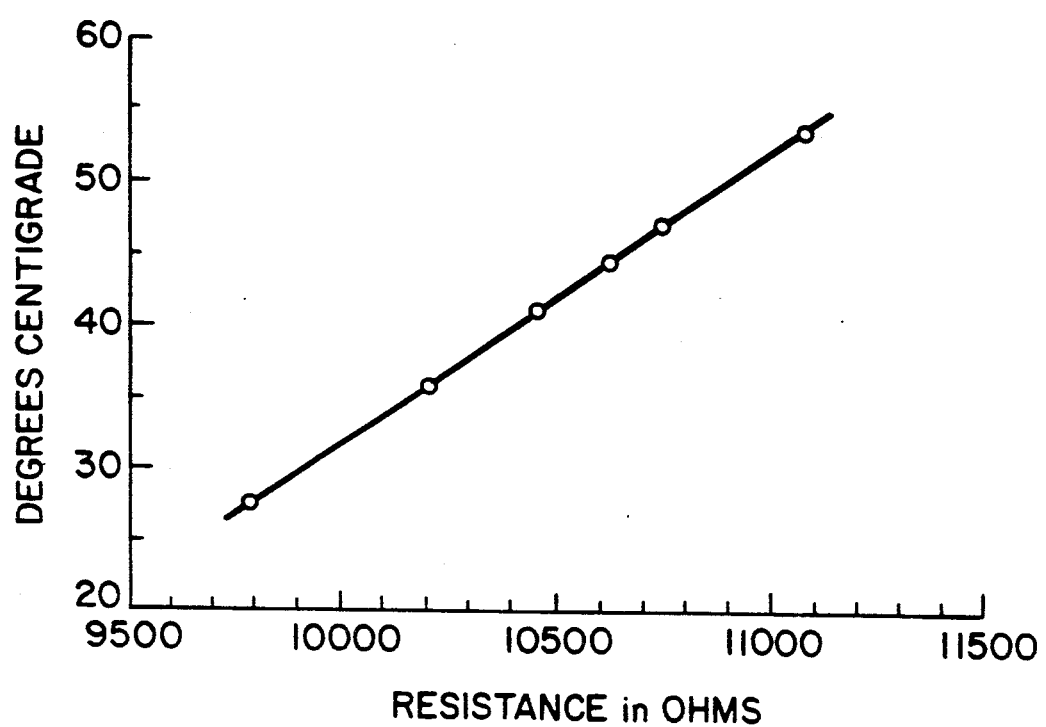
FIG. 7 shows the circuit for measuring oxygen concentration.

A typical thermal sensor response for a nickel resistor 800 Å thick on a glass substrate is shown in FIG. 7.

In use, the probe structure first is calibrated by inserting it into a medium having known oxygen molecule diffusion characteristics and thermal characteristics to produce calibration curves or data.

The measured oxygen values then are correlated with oxygen molecule diffusivity and temperature from the calibration data or curves.

We claim:

1. Apparatus for measuring oxygen partial pressure and temperature at a plurality of locations in tissue and which comprise a thin probe substrate having a cross-sectional area sufficiently small to permit insertion of said thin probe into said tissue, a plurality of oxygen sensors positioned at spatially separated sites along the length of said probe substrate, said oxygen sensors being adapted to measure concentration of oxygen molecules in said tissue, means for correlating said concentration of oxygen molecules with oxygen partial pressure, means for measuring temperature comprising a plurality of temperature sensitive resistors arranged along the length of said probe substrate, at least one of said temperature sensitive resistors being positioned adjacent each of said oxygen sensors, means for passing current through said temperature sensitive resistors, means for measuring voltage drop across said temperature sensitive resistors and means for correlating measured voltage drop with temperature.

2. The apparatus of claim 1 wherein the temperature sensitive resistors are formed from a serpentine thin film of metal to which conductive leads are connected, said leads being connected to said means for measuring a voltage drop across said temperature sensitive resistors.

3. The apparatus of claim 2 wherein the resistors are formed of nickel.

4. The apparatus of claim 1 wherein the resistors are formed of nickel.

5. The apparatus of claim 1 wherein said oxygen sensors comprise a dielectric surface having perforations and metal reactive with oxygen molecules exposed within said perforations.

6. The apparatus of claim 5 wherein said metal reactive with oxygen is selected from the group consisting of gold, palladium and platinum.

7. The apparatus of claim 6 wherein said metal is gold.

* * * * *